United States Patent
Kirsch et al.

[11] Patent Number: 6,057,006
[45] Date of Patent: May 2, 2000

[54] FLUOROCYCLOHEXANE DERIVATIVES, AND LIQUID-CRYSTALLINE MEDIUM

[75] Inventors: Peer Kirsch, Darmstadt; Kazuaki Tarumi, Seeheim; Joachim Krause, Dieburg, all of Germany

[73] Assignee: Merck Patent Gesellschaft, Germany

[21] Appl. No.: 09/090,384

[22] Filed: Jun. 4, 1998

[30] Foreign Application Priority Data

Jun. 4, 1997 [DE] Germany .............. 197 23 275

[51] Int. Cl.$^7$ .................. C09K 19/30; C09K 19/20; C07C 69/76; C07C 19/08; C07C 22/04; C07C 22/08

[52] U.S. Cl. .................. 428/1; 252/299.63; 252/299.66; 252/299.67; 560/62; 560/65; 570/127; 570/129; 570/144; 570/182; 570/184

[58] Field of Search .............. 252/299.61, 299.63, 252/299.66, 299.67; 428/1; 570/127, 129, 143, 144, 182, 184; 560/62, 65

[56] References Cited

U.S. PATENT DOCUMENTS 4,510,069 4/1985 Eidenschink et al. .......... 252/299.61

FOREIGN PATENT DOCUMENTS 5-229979 9/1993 Japan .

OTHER PUBLICATIONS

CAPLUS 1994: 120904.
CAPLUS 1998: 187689.

*Primary Examiner*—Shean C. Wu
*Attorney, Agent, or Firm*—Millen, White, Zelano & Branigan, P.C.

[57] ABSTRACT

The invention relates to fluorocyclohexane derivatives of the formula I

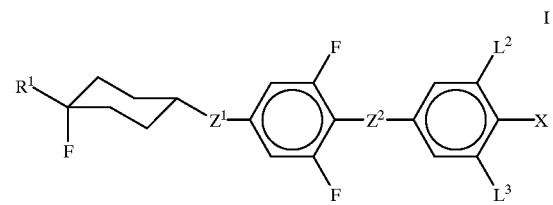

in which $R^1$, $Z^1$, $Z^2$, $L^1$, $L^2$, $L^3$ and X are as defined as below:

X is alkyl or alkoxy having 1 to 10 carbon atoms which is unsubstituted or substituted by halogen, alkenyl or alkenyloxy having 2 to 10 carbon atoms which is unsubstituted or substituted by —CN, —CF$_3$ or —F, or is —CN, —F, —OCHF$_2$, —OCF$_3$, —OCHFCF$_3$ or —OCF$_2$CF$_3$, $L^1$, $L^2$ and $L^3$ are each, independently of one another, H or F, $R^1$ is H, an alkyl or alkenyl radical having 1–12 carbon atoms which is unsubstituted, monosubstituted by CN or CF$_3$ or substituted by halogen, where one or more non-adjacent CH$_2$ groups in these radicals may also, in each case independently of one another, be replaced by —O—, —S—, —CO—, —◊—, —CO—O—, —O—CO— or —O—CO—O—, $Z^1$ and $Z^2$ are each, independently of one another, —CO—O—, —O—CO—, —CH$_2$O—, —O—, —O—CH$_2$—, —CH$_2$CH$_2$—, —CH=CH—, —C≡C— or a single bond, with the proviso that compounds of the formula I in which $L^1$ is H and $Z^2$ is simultaneously a single bond are excluded.

12 Claims, No Drawings

FLUOROCYCLOHEXANE DERIVATIVES, AND LIQUID-CRYSTALLINE MEDIUM

The invention relates to novel fluorocyclohexane derivatives of the formula I

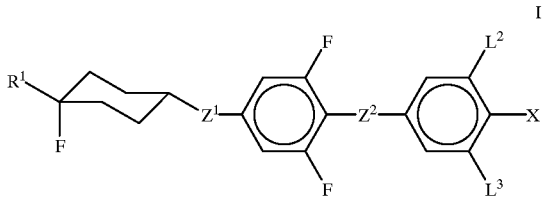

in which x is alkyl or alkoxy having 1 to 10 carbon atoms which is unsubstituted or at least monosubstituted by halogen, alkenyl or alkenyloxy having 2 to 10 carbon atoms which is unsubstituted or at least monosubstituted by —CN, —CF$_3$ or —F, or is —CN, —F, —OCHF$_2$, —OCF$_3$, —OCHFCF$_3$ or —OCF$_2$CF$_3$, L$^1$, L$^2$ and L$^3$ are each, independently of one another, H or F, R$^1$ is H, an alkyl or alkenyl radical having 1–12 carbon atoms which is unsubstituted, monosubstituted by CN or CF$_3$ or at least monosubstituted by halogen, where one or more non-adjacent CH$_2$ groups in these radicals may also, in each case independently of one another, be replaced by —O—, —S—, —CO—,

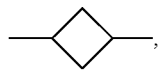

—CO—O—, —O—CO— or —O—CO—O—,

Z$^1$ and Z$^2$ are each, independently of one another, —CO—O—, —O—CO—, —CH$_2$O—, —O—, —O—CH$_2$—, —CH$_2$CH$_2$—, —CH=CH—, —C≡C— or a single bond, with the proviso that compounds of the formula I in which L$^1$ is H and Z$^2$ is simultaneously a single bond are excluded.

In addition, the invention relates to the use of compounds of the formula I as components of liquid-crystalline media, and to liquid-crystal and electro-optical display elements which contain the liquid-crystalline media according to the invention.

The compounds of the formula I can be used as components of liquid-crystalline media, in particular for displays based on the principle of the twisted cell, the guest-host effect, the effect of deformation of aligned phases (DAP) or electrically controlled birefringence (ECB), or the effect of dynamic scattering. The substances employed hitherto for this purpose all have certain disadvantages, for example inadequate stability to exposure to heat, light or electric fields, or unfavourable elastic and/or dielectric properties.

Compounds containing fluorocyclohexane units are disclosed, for example, in JP 05125002, JP 05229979 and EP 0107759, but no compounds additionally having lateral fluorine substituents on a central phenyl ring are described therein. Although the compounds excluded by the proviso are covered by GB 2248059, the subject-matter of this document is directed toward compounds of low viscosity and high dielectric anisotropy.

The invention had the object of finding novel, stable, liquid-crystalline or mesogenic compounds having a comparatively high clearing point and low positive or negative dielectric anisotropy which are suitable as components of liquid-crystalline media, in particular for TFT and STN displays.

It has now been found that the compounds of the formula I are eminently suitable as components of liquid-crystalline media. They can be used to obtain stable liquid-crystalline media, particularly suitable for TFT or STN displays. The novel compounds are distinguished, in particular, by high thermal stability, which is advantageous for a high holding ratio, and exhibit high clearing point values compared with cyclohexane derivatives containing no axial fluorine. A preferred group of compounds of the formula I has negative or low positive dielectric anisotropy and are therefore particularly suitable for displays based on the effect of deformation of aligned phases.

The provision of compounds of the formula I very generally considerably broadens the range of liquid-crystalline substances which are suitable from various applicational points of view for the preparation of liquid-crystalline mixtures.

The compounds of the formula I have a broad range of applications. Depending on the choice of substituents, these compounds can be used as base materials of which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity. The definition of the formula I includes all isotopes of the chemical elements bonded therein.

In the pure state, the compounds of the formula I are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media containing at least one compound of the formula I, and to liquid-crystal display elements, in particular electro-optical display elements, which contain media of this type.

Above and below, R$^1$, Z$^1$, Z$^2$, L$^1$, L$^2$, L$^3$ and X are as defined above, unless expressly stated otherwise.

The following group of compounds of the subformulae I1 to I9 represents a preferred embodiment of the invention:

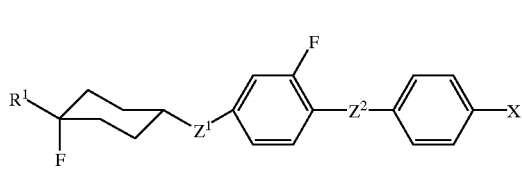

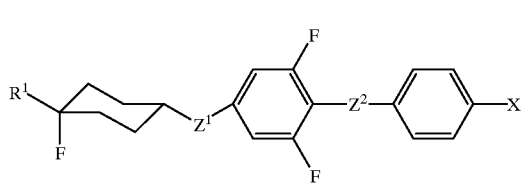

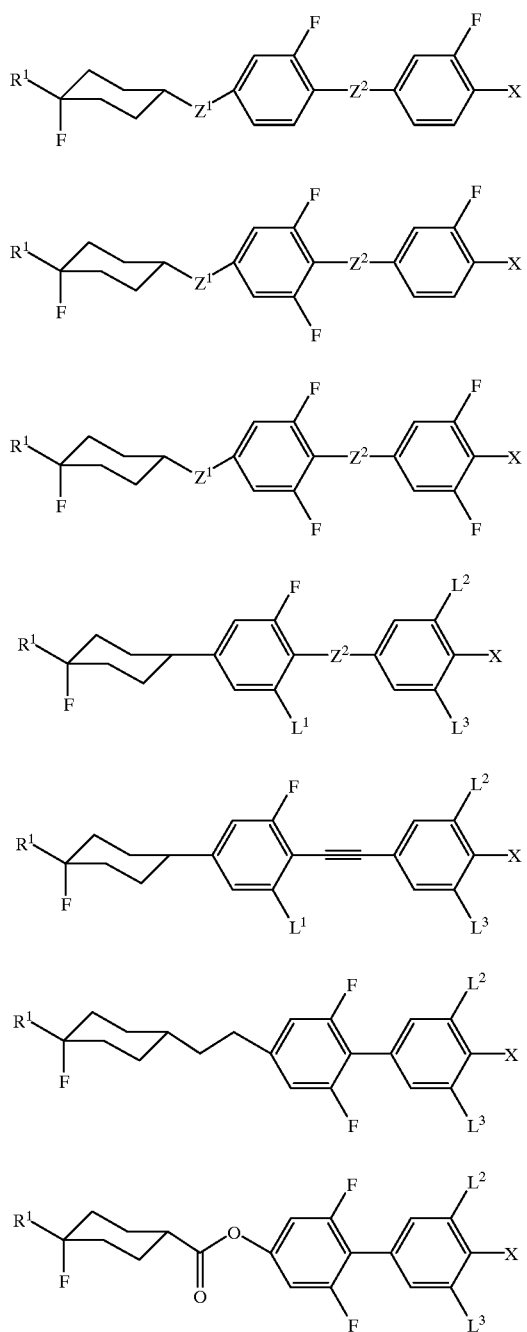

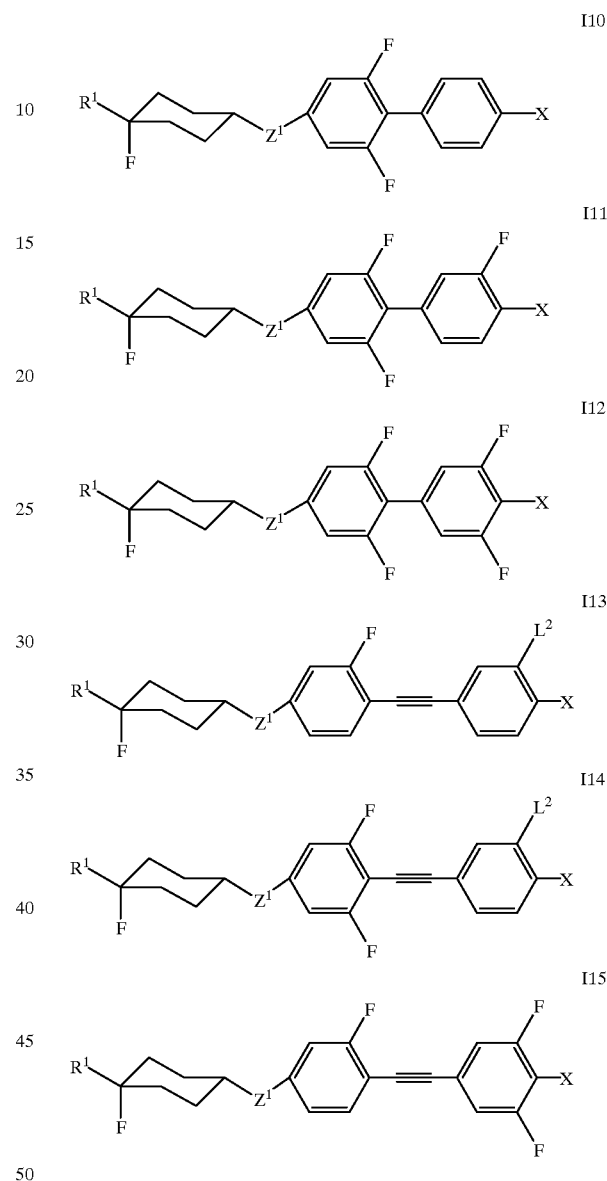

in which $R^1$, $L^1$, $L^2$, $L^3$, $Z^1$, $Z^2$ and X are as defined above.

$Z^1$ is preferably a single bond or —CH$_2$—CH$_2$—, in particular —CH$_2$—CH$_2$—, $Z^2$ is preferably a single bond, triple bond or —CH$_2$—CH$_2$—, in particular a single or triple bond. X is preferably unsubstituted alkyl or alkoxy having 1 to 7 carbon atoms, unsubstituted or at least monofluoro-substituted alkenyl or alkenyloxy having 2 to 7 carbon atoms, F, CN, OCF$_3$ or OCHF$_2$, particularly preferably alkyl, alkoxy, F or CN, very particularly preferably alkyl or F.

In the compounds of the formulae above and below $R^1$ is preferably straight-chain alkyl having 1 to 10 carbon atoms or alkenyl having 2 to 10 carbon atoms, furthermore preferably alkoxy having 1 to 10 carbon atoms.

Preference is furthermore given to compounds of the formula I in which $L^1$ and $L^2$ are simultaneously F, while $Z^1$ is a single bond or —CH$_2$—CH$_2$—.

Particular preference is furthermore given to the compounds of the formulae I10 to I15 in the following group:

in which $R^1$, $Z^1$, $L^2$ and X are as defined above.

If $R^1$ in the formulae above and below is an alkyl radical and/or alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ is an alkyl radical in which one CH$_2$ group has been replaced by —CH═CH—, this can be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If $R^1$ is an alkyl radical in which one $CH_2$ group has been replaced by —O— and one has been replaced by —CO—, these are preferably adjacent. These thus contain one acyloxy group —CO—O— or one oxycarbonyl group —O—CO—. These are preferably straight-chain and have 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If $R^1$ is an alkyl radical in which one $CH_2$ group has been replaced by unsubstituted or substituted —CH=CH— and an adjacent $CH_2$ group has been replaced by CO or CO—O or O—CO—, this can be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl and 9-methacryloyloxynonyl.

If $R^1$ is an alkyl or alkenyl radical which is monosubstituted by CN or $CF_3$, this radical is preferably straight-chain, and the substitution by CN or $CF_3$ is in the ω-position.

If $R^1$ is an alkyl or alkenyl radical which is at least monosubstituted by halogen, this radical is preferably straight-chain, and halogen is preferably F or Cl. In the case of multiple substitution, halogen is preferably F. The resulting radicals also include perfluorinated radicals. In the case of monosubstitution, the fluorine or chlorine substituent can be in any desired position, but is preferably in the ω-position.

Compounds of the formula I containing branched wing groups $R^1$ nay occasionally be of importance due to better solubility in the customary liquid-crystalline base materials, but in particular as chiral dopes if they are optically active. Smectic compounds of this type are suitable as components for ferroelectric materials.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

The formula I covers the racemates of these compounds and the optical antipodes, and mixtures thereof.

Of these compounds of the formula I and the subformulae, preference is given to those in which at least one of the radicals present therein has one of the preferred meanings indicated.

Some very particularly preferred compounds of the formula I are those of the subformulae I16 to I24:

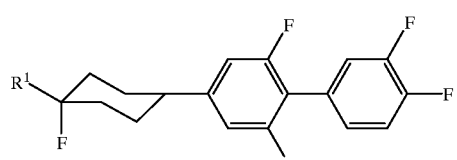
I16

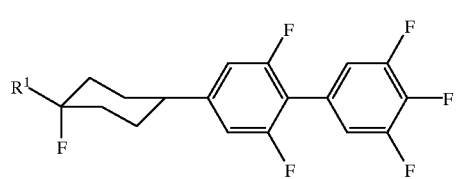
I17

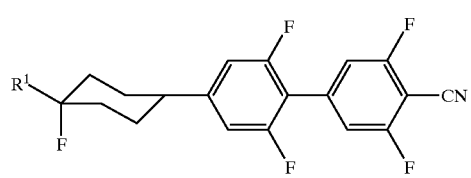
I18

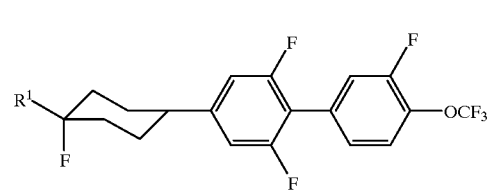
I19

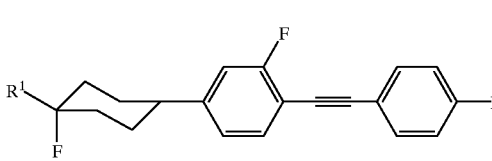
I20

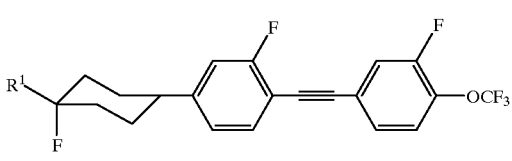
I21

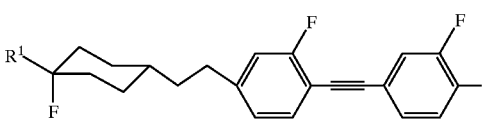
I22

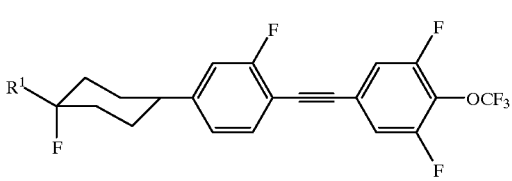
I23

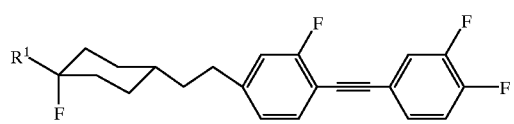

I24 in which R¹ is as defined above and X' is alkyl or alkoxy having 1 to 10 carbon atoms.

Very particularly preferred compounds from this group are those of the formulae I16, I17, I20 and I24.

The compounds of the formula I are prepared by methods known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions.

Use can also be made here of variants which are known per se, but are not described here in greater detail.

The novel axially fluorinated compounds of the formula I can be synthesized by using hydrogen fluoride under pressure or by means of amine/hydrogen fluoride adducts (for example A. V. Grosse, C. B. Linn, J. Org. Chem. 3, (1938) 26; G. A. Olah, M. Nojima, I. Kerekes, Synthesis, (1973) 779); G. A. Olah, X -Y. Li, Q. Wang, G. K. S. Prakash, Synthesis (1993) 693). Cross-coupling reactions can be carried out as described in DE 4220082.

Scheme 1

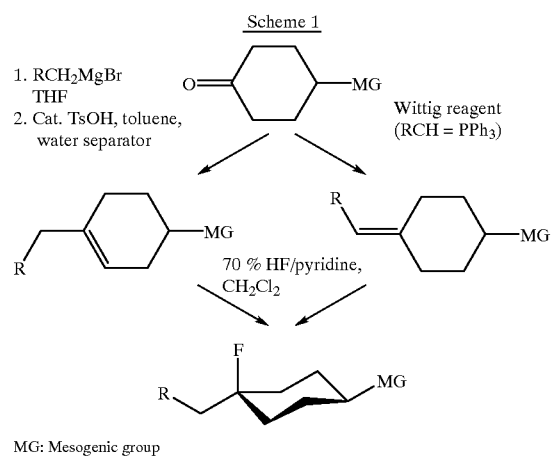

MG: Mesogenic group

Scheme 2

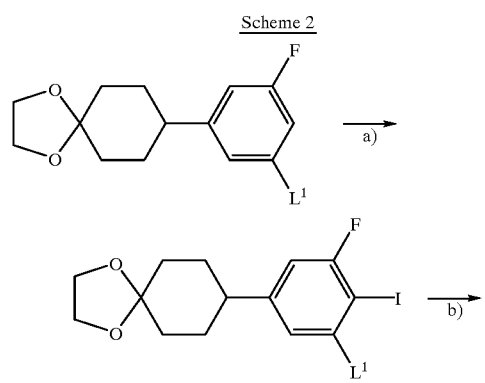

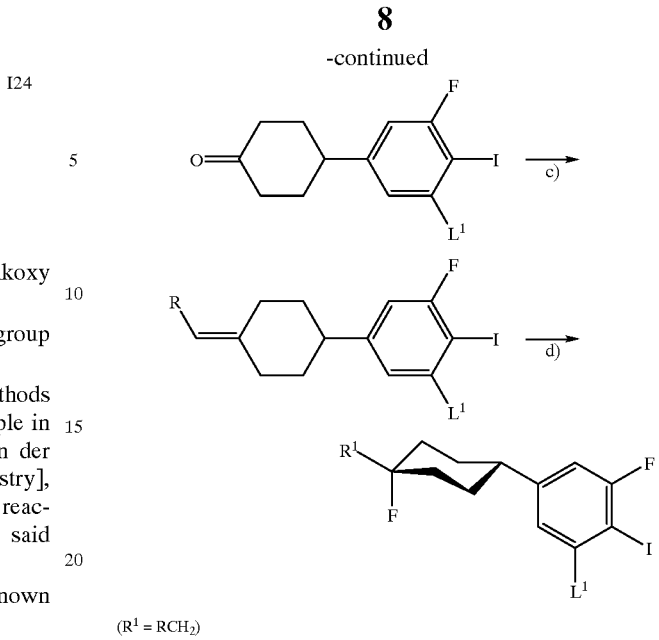

(R¹ = RCH₂)

a) 1. L¹=H: BuLi, KOtBu, THF; L¹=F: BuLi, THF;
   2. I2, THF
b) HCOOH, toluene
c) RCH₂PPh₃+Br⁻, KOtBu, THF
d) 70% HF/pyridine, CH₂Cl₂

Scheme 3

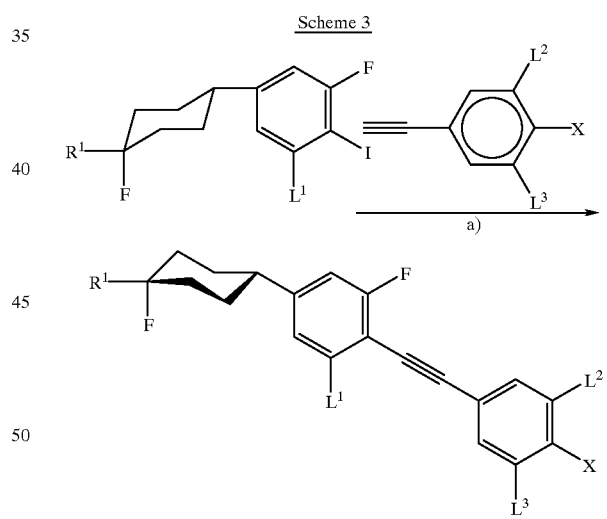

a) NEt₃, cat. CuI, cat. PdCl₂(PPh₃)₂

Scheme 4

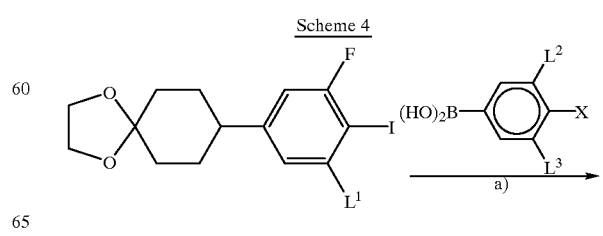

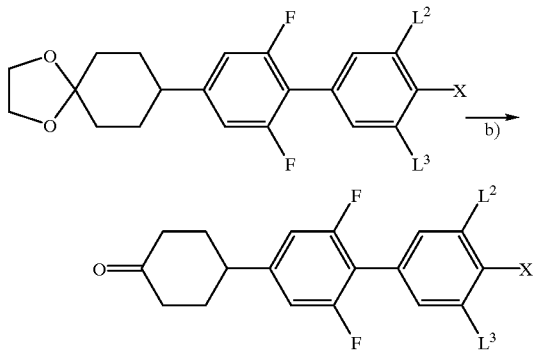

a) Na$_2$CO$_3$/Pd(PPh$_3$)$_4$
b) HCOOH, toluene

Scheme 5

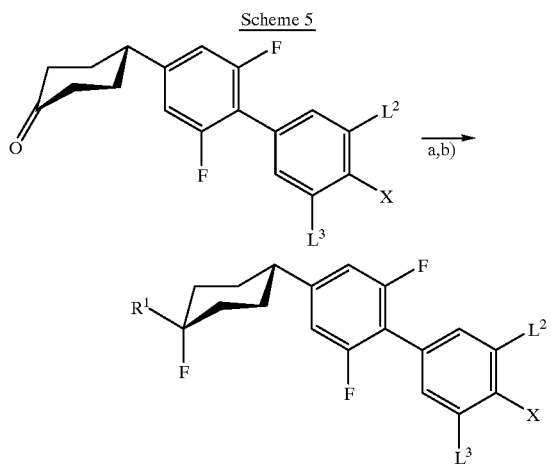

a) RCH$_2$PPh$_3$+Br$^-$, KOtBu, THF
b) 70% HF/pyridine, CH$_2$Cl$_2$

Esters of the formula I can also be obtained by esterification of corresponding carboxylic acids (or reactive derivatives thereof) using alcohols or phenols (or reactive derivatives thereof) or by the DCC method (DCC=dicyclohexylcarbodiimide).

The corresponding carboxylic acids and alcohols or phenols are known or can be prepared analogously to known processes.

In a further process for the preparation of compounds of the formula I in which Z$^1$ or Z$^2$ is —CH═CH—, an aryl halide is reacted with an olefin in the presence of a tertiary amine and in the presence of a palladium catalyst (cf. R. F. Heck, Acc. Chem. Res. 12 (1979) 146). Examples of suitable aryl halides are chlorides, bromides and iodides, in particular bromides and iodides. The tertiary amines which are necessary for the success of the coupling reaction, such as, for example, triethylamine, are also suitable as solvent.

Examples of suitable palladium catalysts are palladium salts, in particular Pd(II) acetate, and organophosphorous (III) compounds, such as, for example, triarylphosphines. Reaction can be carried out in the presence or absence of an inert solvent, at temperatures between 0° C. and 150° C., preferably between 20° C. and 100° C.; examples of suitable solvents are nitriles, such as acetonitrile, or hydrocarbons, such as benzene or toluene. The aryl halides and olefins employed as starting materials are frequently commercially available or can be prepared by processes known from the literature, for example by halogenation of corresponding parent compounds or by elimination reactions on corresponding alcohols or halides.

In this way, for example, stilbene derivatives can be prepared. Stilbenes can furthermore be prepared by reacting a 4-substituted benzaldehyde with a corresponding phosphorous ylide by the Wittig method. However, it is also possible to prepare tolans of the formula I by using monosubstituted acetylene instead of the olefin (Synthesis 627 (1980) or Tetrahedron Lett. 27, 1171 (1986)).

Furthermore, the coupling of aromatic compounds can be carried out by reacting aryl halides with aryltin compounds. These reactions are preferably carried out with addition of a catalyst, such as, for example, a palladium(0) complex, in inert solvents, such as hydrocarbons, at high temperatures, for example in boiling xylene under a protective gas.

Coupling reactions of alkynyl compounds with aryl halides can be carried out analogously to the process described by A. O. King, E. Negishi, F. J. Villani and A. Silveira in J. Org. Chem. 43, 358 (1978).

Tolans of the formula I in which Z$^2$ is —C≡C— can also be prepared by Fritsch-Buttenberg-Wiechell rearrangement (Ann. 279, 319, 1984), in which 1,1-diaryl-2-haloethylenes are rearranged in the presence of strong bases to give diarylacetylenes.

Tolans of the formula I can also be prepared by brominating the corresponding stilbenes, and then subjecting the products to dehydrohalogenation. Use can also be made here of variants of this reaction which are known per se, but are not mentioned here in greater detail.

Ethers of the formula I are obtainable by esterification of corresponding hydroxyl compounds, preferably corresponding phenols, where the hydroxyl compound is advantageously first converted into a corresponding metal derivative, for example into the corresponding alkali metal alkoxide or alkali metal phenoxide by treatment with NaH, NaNH$_2$, NaOH, KOH, Na$_2$CO$_3$ or K$_2$CO$_3$. This alkoxide or phenoxide can then be reacted with the appropriate alkyl halide, alkyl sulfonate or dialkyl sulfate, advantageously in an inert solvent, such as, for example, acetone, 1,2-dimethoxyethane, DMF or dimethyl sulfoxide, or alternatively with an excess of aqueous or aqueous-alcoholic NaOH or KOH, at temperatures between about 20° C. and 100° C.

The starting materials are either known or can be prepared analogously to known compounds.

The liquid-crystalline media according to the invention preferably comprise from 2 to 40, in particular from 4 to 30, components as further constituents besides one or more compounds according to the invention. These media very particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)-ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated. For reasons of simplicity, Cyc below denotes a 1,4-cyclohexylene radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical and Bco denotes a bicyclo[2.2.2]octylene radical, where Cyc and/or Phe may be unsubstituted or monosubstituted or polysubstituted by Cl, F or CN.

The most important compounds suitable as further constituents of media according to the invention can be characterized by the formulae 1, 2, 3, 4 and 5:

| | |
|---|---|
| R'—L'E—R" | 1 |
| R'—L—COO—E—R" | 2 |
| R'—L—OOC—E—R" | 3 |
| R'—L—CH$_2$CH$_2$—E—R" | 4 |
| R'—L—C≡C—E—R" | 5 |

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

In formulae 1, 2, 3, 4 and 5, R' is in each case, independently of one another, alkyl, alkenyl, alkoxy, alkoxyalkyl, alkenyloxy or alkanoyloxy having up to 8 carbon atoms and R" is in each case, independently of one another, alkyl, alkenyl, alkoxy, alkoxyalkyl, alkenyloxy or alkanoyloxy having up to 8 carbon atoms, F, Cl, CN, NCS or (O)$_i$CH$_{3-(r+s)}$F$_r$Cl$_s$, where i is 0 or 1, and r and s are 1, 2 or 3.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" are in each case, independent of one another, alkyl, alkenyl, alkoxy, alkoxyalkyl, alkenyloxy or alkanoyloxy having up to 8 carbon atoms. This smaller sub-group is called group A below, and the compounds are labeled with the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is known as group B, R" is —F, —Cl, —NCS or —(O)$_i$CH$_{3-(r+s)}$F$_r$Cl$_s$, where i is 0 or 1, and r and s are 1, 2 or 3; the compounds in which R" has this meaning are labeled with the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is known as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably comprise one or more compounds selected from group A and/or group B and/or group C. The proportions by weight of the compounds from these groups in the media according to the invention are preferably Group A: from 0 to 90%, preferably from 20 to 90%, in particular from 30 to 90%

Group B: from 0 to 80%, preferably from 10 to 80%, in particular from 10 to 65%

Group C: from 0 to 80%, preferably from 5 to 80%, in particular from 5 to 50%, the sum of the proportions by weight of the group A and/or B and/or C compounds present in the particular media according to the invention preferably being 5%–90% and in particular from 0% to 90%.

The media according to the invention preferably comprise from 1 to 40%, particularly preferably from 5 to 30%, of compounds according to the invention. Further preferred media are those which comprise more than 40%, in particular from 45 to 90%, of compounds according to the invention. The media preferably comprise three, four or five compounds according to the invention.

A very particularly preferred embodiment of the invention is a liquid-crystalline medium based on a mixture of polar compounds of negative dielectric anistropy which comprises at least one compound of the formula I

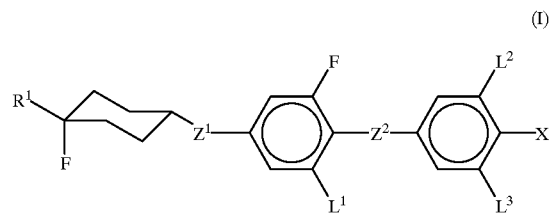

(I)

in which R$^1$, Z$^1$, Z$^2$, L$^1$, L$^2$, L$^3$ and X are as defined above, in particular additionally comprising one or more compounds of the formula II

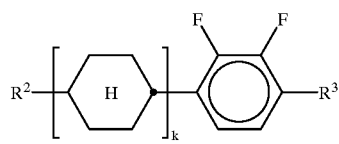

(II)

in which $R^2$ and $R^3$ are each, independently of one another, H, an unsubstituted alkyl or alkenyl radical having up to 18 carbon atoms, in which one or more non-adjacent $CH_2$ groups may be replaced by a radical selected from the group consisting of —O—, —S— and —C≡C—, and k is 1 or 2,
in particular for electrooptical displays having active-matrix addressing based on the ECB effect.

Preferred embodiments are the following:
a) A medium which additionally comprises one or more compounds of the formula III:

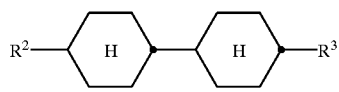

(III)

in which $R^2$ and $R^3$ are as defined above.
b) A medium which essentially consists of 4 or more compounds selected from the formulae I and II, and two or more compounds of the formula III.
c) A medium which comprises at least 2 compounds of the formula I.
d) A medium in which the proportion of compounds of the formula I in the mixture as a whole is at least 15% by weight.
e) A medium in which the proportion of compounds of the formula II in the mixture as a whole is at least 30% by weight.
f) A medium in which the proportion of compounds of the formula III in the mixture as a whole is from 10 to 50% by weight.
g) A liquid-crystalline medium comprising at least 2 compounds selected from the formulae IIIa and IIIb

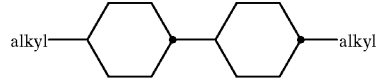

(IIIa)

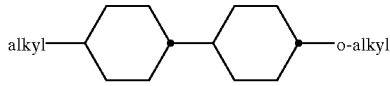

(IIIb)

in which
alkyl is $C_{1-6}$-alkyl,
in particular comprising 1 compound of the formula IIIa and at least 1 compound of the formula IIIb.
h) A liquid-crystalline medium essentially consisting of:
15–30% by weight of one or more compounds of the formula I,
30–70% by weight of one or more compounds of the formula II and
10–50% by weight of one or more compounds of the formula III.

The liquid-crystal mixture preferably has a nematic phase range of at least 60 K and a maximum viscosity of 30 mpa.s at 20° C.

The liquid-crystal mixture according to the invention preferably has a Δε of from about −0.5 to −5, in particular from about −3.0 to −4.5, where Δε denotes the dielectric anisotropy.

The birefringence Δn in the liquid-crystal mixture is preferably between 0.04 and 0.10, particularly preferably between 0.05 and 0.09, and/or the dielectric constant $e_\parallel$ is preferably greater than or equal to 3, in particular from 3.2 to 8.5.

In a further preferred embodiment, the media according to the invention comprise
at least one compound of the formula I,
at least one compound of the formula II, and
at least one compound selected from the formulae V to IX

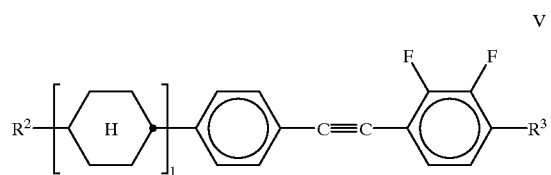

V

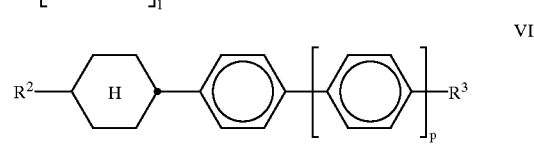

VI

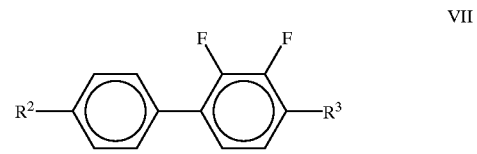

VII

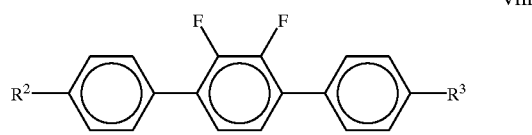

VIII

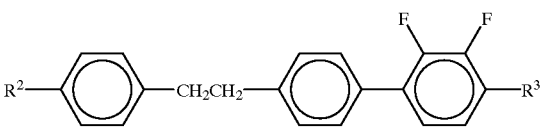

IX in which
$R^2$ and $R^3$ are as defined above, and
l and p are each, independently one another, 0 or 1.
In particular, these media essentially consist of
one or more compounds of the formula I,
one or more compounds of the formula II,
one or more compounds of the formulae V to IX, and
one or more compounds of the formula VI.

Media comprising compounds of the formula V in which l is 0 and compounds of the formula V in which l is 1 are particularly preferred.

Media comprising one or more compounds of the formulae V to IX generally have birefringence values of between 0.10 and 0.20, preferably between 0.11 and 0.16.

In a particularly preferred embodiment, the media according to the invention essentially consist of 10–25% by weight of one or more compounds of the formula I,
20–40% by weight of one or more compounds of the formula II,
20–40% by weight of one or more compounds of the formula V and
15–35% by weight of one or more compounds of the formula VI.

The dielectrics may also comprise further additives known to the person skilled in the art and described in the literature. For example, 0–15% of pleochroic dyes can be added, furthermore conductive salts, preferably ethyldimethyldodecylammonium 4-hexyloxybenzoate, tetrabutylammonium tetraphenylboranate or complex salts of crown ethers (cf., for example, Haller et al., Mol. Cryst. Liq. Cryst. Volume 24, pages 249–258 (1973)) can be added to improve the conductivity or substances can be added to modify the dielectric anistropy, the viscosity and/or the alignment of the nematic phases. Such substances are described, for example, in DE-A 22 09 127, 22 40 864, 23 21 632, 23 38 281, 24 50 088, 26 37 430 and 28 53 728.

The individual components of the formula II to VI in the liquid-crystal phases according to the invention are either known or their methods of preparation can easily be derived by the person skilled in the relevant art since they are based on standard methods described in the literature.

Corresponding compounds of the formula II are described, for example, in WO 89-08633.

Corresponding compounds of the formula III are described, for example, in DE 33 21 373.

Corresponding compounds of the formula V are described in WO 88/07514.

The compounds of the formula VI are known, for example from DE 26 36 684 (p=0) or DE 29 27 277 (p=1).

In a further preferred embodiment, the nematic liquid-crystal mixtures of the displays according to the invention preferably comprise at least 10% of compounds of the formula I, particularly preferably from 15 to 30% of compounds of the formula I.

The nematic liquid-crystal mixtures in the displays according to the invention generally comprise two components A and B, which themselves consist of one or more individual compounds.

Component A has significantly negative dielectric anistropy and gives the nematic phase a dielectric anisotropy of $\leq -0.3$. It preferably comprises compounds of the formulae I and II.

The proportion of component A is preferably between 45 and 100%.

For component A, one (or more) individual compounds which have a $\Delta\epsilon$ value of $\leq -0.8$ is preferably selected. This value must be more negative the smaller the proportion of A in the mixture as a whole.

Component B preferably has pronounced nematogeneity and a viscosity of not greater than 30 mm$^2$s$^{-1}$, preferably not more than 25 mm$^2$s$^{-1}$ at 20° C.

Particularly preferred individual compounds of component B are extremely low-viscosity nematic liquid crystals having a viscosity of not greater than 18 mm$^2$s$^{-1}$, preferably not more than 12 mm$^2$s$^{-1}$, at 20° C. Component B is monotropically or enantiotropically nematic, has no smectic phases and can prevent the occurrence of smectic phases in liquid-crystal mixtures down to very low temperatures. For example, if various materials of high nematogeneity are added to a smectic liquid-crystal mixture, the nematogeneity of these materials can be compared through the resultant degree of suppression of smectic phases.

A large number of suitable materials are known to the person skilled in the art from the literature. Particular preference is given to compounds of the formula III.

The phases preferably comprise from 4 to 15, in particular from 5 to 12, compounds of the formulae I, II and III, or I, II, V and VI.

The media according to the invention may furthermore comprise one or more dyes.

The structure of the liquid-crystal displays according to the invention corresponds to the conventional geometry, as described, for example, in EP-A 0 240 379.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

The examples below are intended to illustrate the invention without representing a limitation. Above and below, percent data are percent by weight. All temperatures are given in degrees Celsius. m.p.=melting point, cl.p.=clearing point. Furthermore, C=crystalline state, N=nematic phase, S=smectic phase and I=isotropic phase. The number between two symbols indicates the conversion temperature in degrees Celsius. $\Delta n$ denotes optical anisotropy (589 nm, 20° C.) and $\Delta\epsilon$ denotes the dielectric anisotropy (1 kHz, 20° C.). The viscosity (mm$^2$/sec) was determined at 20° C.

"Conventional work-up" means that water is added if necessary, the mixture is extracted with methylene chloride, diethyl ether, or toluene, the organic phase is separated off, dried and evaporated, and the product is purified by distillation under reduced pressure or crystallization and/or chromatography.

The following abbreviations are used:

| THF | tetrahydrofuran |
|---|---|
| KOtBu | potassium tert-butoxide |
| RT | room temperature |

In the examples below, the structures of the liquid-crystal compounds are indicated by acronyms, the transformation into chemical formulae taking place in accordance with Tables A and B below. All radicals $C_nH_{2n+1}$ and $C_mH_{2m+1}$ are straight-chain alkyl radicals having n and m carbon atoms respectively. The alkenyl radicals have the trans-configuration. The coding in Table B is self-evident. In Table A, only the acronym for the parent structure is indicated. In individual cases, the acronym for the parent structure is followed, separated by a hyphen, by a code for the substituents $W^1$, $W^2$, $Q^1$ $Q^2$ and $Q^3$.

| Code for $W^1$, $W^2$, $Q^1$, $Q^2$, $Q^3$ | $W^1$ | $W^2$ | $Q^1$ | $Q^2$ | $Q^3$ |
|---|---|---|---|---|---|
| nm | $C_nH_{2n+1}$ | $C_mH_{2m+1}$ | H | H | H |
| nOm | $C_nH_{2n+1}$ | $OC_mH_{2m+1}$ | H | H | H |
| nO.m | $OC_nH_{2n+1}$ | $C_mH_{2m+1}$ | H | H | H |
| n | $C_nH_{2n+1}$ | CN | H | H | H |
| nN.F | $C_nH_{2n+1}$ | CN | H | H | F |
| nF | $C_nH_{2n+1}$ | F | H | H | H |
| nOF | $OC_nH_{2n+1}$ | F | H | H | H |
| nCl | $C_nH_{2n+1}$ | Cl | H | H | H |
| nF.F | $C_nH_{2n+1}$ | F | H | H | F |
| nmF | $C_nH_{2n+1}$ | $C_mH_{2m+1}$ | H | F | H |
| $nCF_3$ | $C_nH_{2n+1}$ | $CF_3$ | H | H | H |
| $nOCF_3$ | $C_nH_{2n+1}$ | $OCF_3$ | H | H | H |
| $nOCF_2$ | $C_nH_{2n+1}$ | $OCHF_2$ | H | H | H |
| nS | $C_nH_{2n+1}$ | NCS | H | H | H |
| rVsN | $C_nH_{2n+1}$—CH=CH—$C_9H_{2a}$— | CN | H | H | H |
| rEsN | $C_nH_{2n+1}$—O—$C_2H_{2a}$— | CN | H | H | H |
| nNF | $C_nH_{2n+1}$ | CN | H | F | H |
| nAm | $C_nH_{2n+1}$ | $COOC_mH_{2m+1}$ | H | H | H |
| nCl.F | $C_nH_{2n+1}$ | Cl | H | H | F |
| n-Vm | $C_nH_{2n+1}$ | —CH=CH—$C_mH_{2m+1}$ | H | H | H |
| nV-Vm | $C_nH_{2n+1}$—CH=CH— | —CH=CH—$C_mH_{2m+1}$ | H | H | H |
| nV-m | $C_nH_{2n+1}$—CH=CH— | —$C_mH_{2m+1}$ | H | H | H |
| nV-Om | $C_nH_{2n+1}$—CH=CH— | —$OC_mH_{2m+1}$ | H | H | H |
| n-OMT | $C_nH_{2n+1}$ | —OCHF—$CF_3$ | H | H | H |
| nV-N | $C_nH_{2n+1}$—CH=CH— | —CN | H | H | H |
| nV-F | $C_nH_{2n+1}$—CH=CH— | F | H | H | H |
| nV-F.F | $C_nH_{2n+1}$—CH=CH— | F | H | H | F |
| n-2Vm | $C_nH_{2n+1}$ | $C_mH_{2m+1}$—CH=CH—$CH_2CH_2$— | H | H | H |

The TN and STN displays preferably contain liquid-crystalline mixtures composed of one or more compounds from Tables A and B.

TABLE A ($Q^1$, $Q^2$, $Q^3$ = H or F)

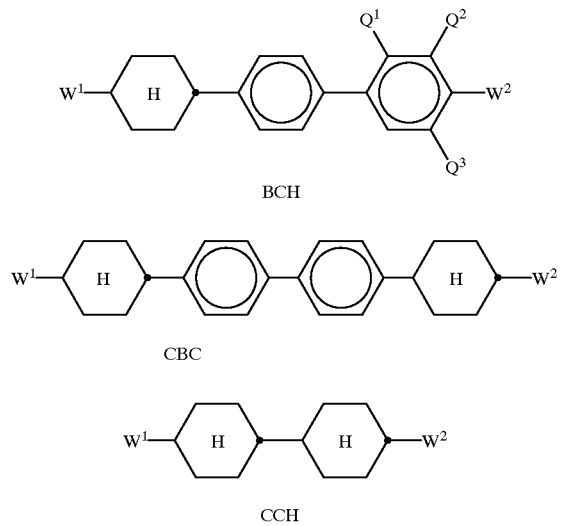

BCH

CBC

CCH

CCP

TABLE A-continued ($Q^1$, $Q^2$, $Q^3$ = H or F)

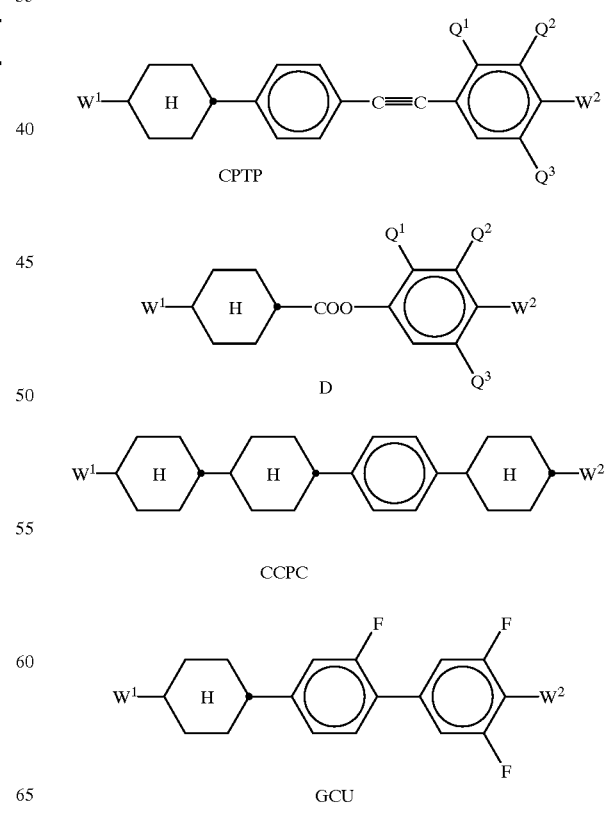

CPTP

D

CCPC

GCU

TABLE A-continued
($Q^1$, $Q^2$, $Q^3$ = H or F)
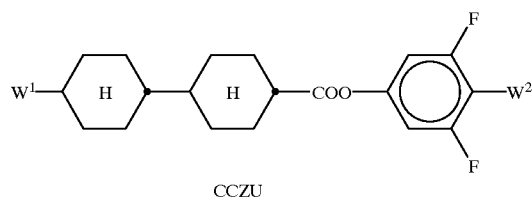
CCZU
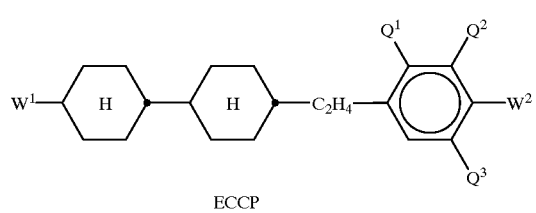
ECCP
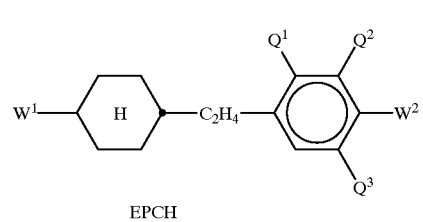
EPCH
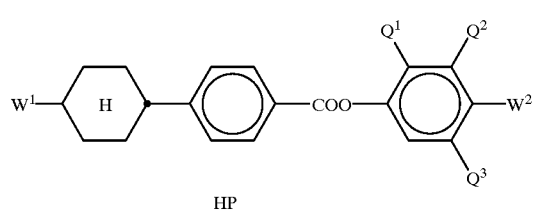
HP
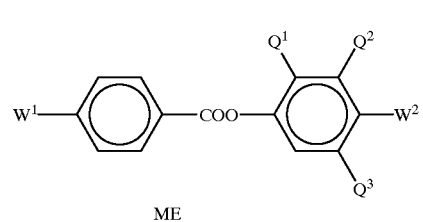
ME
TABLE A-continued
($Q^1$, $Q^2$, $Q^3$ = H or F)
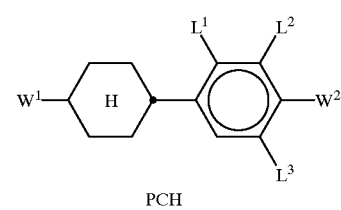
PCH
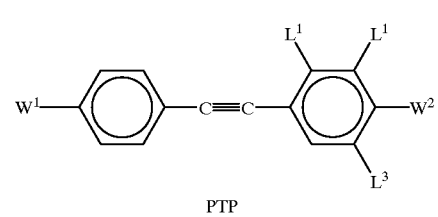
PTP
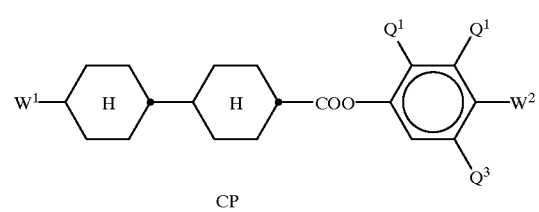
CP
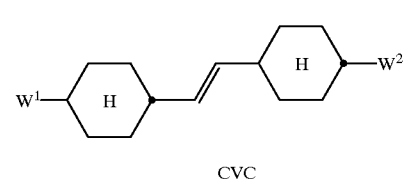
CVC
TABLE B
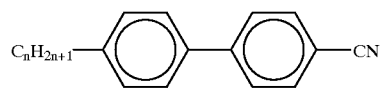
K3n
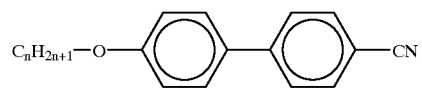
M3n
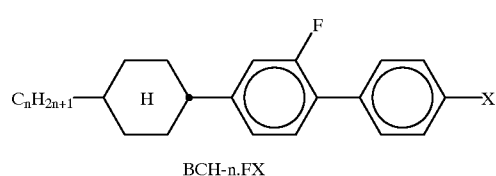
BCH-n.FX

TABLE B-continued
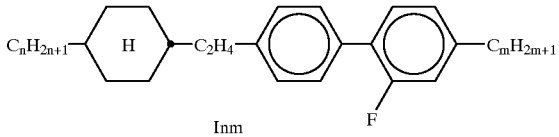
Inm
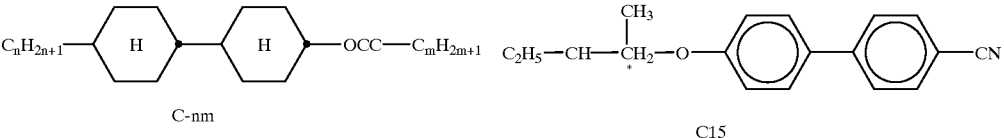
C-nm
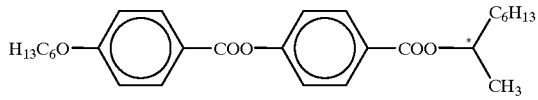
C15
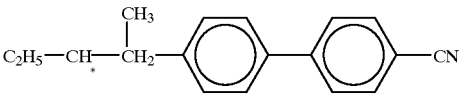
S-811
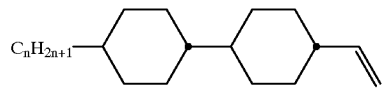
CB15
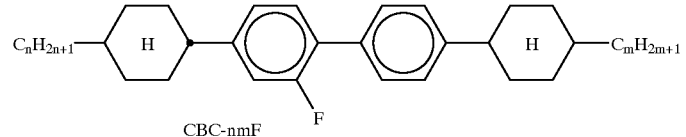
CC-n-V
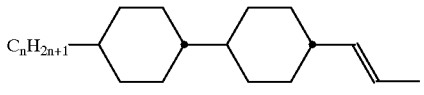
CBC-nmF
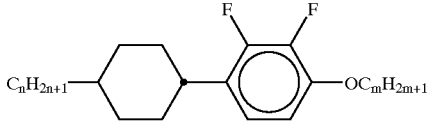
CC-n-V1
ECB mixtures preferably comprise one or more components from Table C:
TABLE C
PCHnOmFF
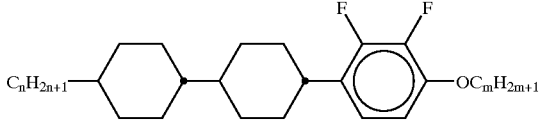
CCPnOmFF
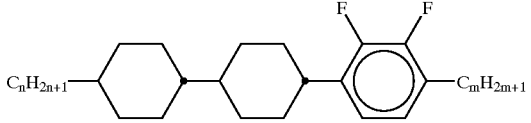
CCPnmFF TABLE C-continued

| Code | Structure |
|---|---|
| D-nOmFF | $C_nH_{2n+1}$–[Cy]–COO–[Ph(2,3-F,F)]–$OC_mH_{2m+1}$ |
| CBCnmF | $C_nH_{2n+1}$–[Cy]–[Ph(F)]–[Ph]–[Cy]–$C_mH_{2m+1}$ |
| CCHnOm | $C_nH_{2n+1}$–[Cy]–[Cy]–$OC_mH_{2m+1}$ |
| CCHnm | $C_nH_{2n+1}$–[Cy]–[Cy]–$C_mH_{2m+1}$ |
| CPnOmFF | $C_nH_{2n+1}$–[Cy]–[Cy]–COO–[Ph(2,3-F,F)]–O–$OC_mH_{2m+1}$ |
| CHnm | $C_nH_{2n+1}$–[Cy]–[Cy]–COO–[Cy]–$C_mH_{2m+1}$ |
| BCNnm | $C_nH_{2n+1}$–[Cy]–[Cy(CN)]–[Cy]–$C_mH_{2m+1}$ |
| PTP-nOm | $C_nH_{2n+1}$–[Ph]–C≡C–[Ph(2,3-F,F)]–$OC_mH_{2m+1}$ |
| CPTP-nOm | $C_nH_{2n+1}$–[Cy]–[Ph]–C≡C–[Ph(2,3-F,F)]–$OC_mH_{2m+1}$ |
| PCH-nOm | $C_nH_{2n+1}$–[Cy]–[Ph]–$OC_mH_{2m+1}$ |
| PCH-nm | $C_nH_{2n+1}$–[Cy]–[Ph]–$C_mH_{2m+1}$ |
| BCH-nm | $C_nH_{2n+1}$–[Cy]–[Ph]–[Ph]–$C_mH_{2m+1}$ |

TABLE C-continued

T-nFFm

B-nOmFF

ET-nOmFF

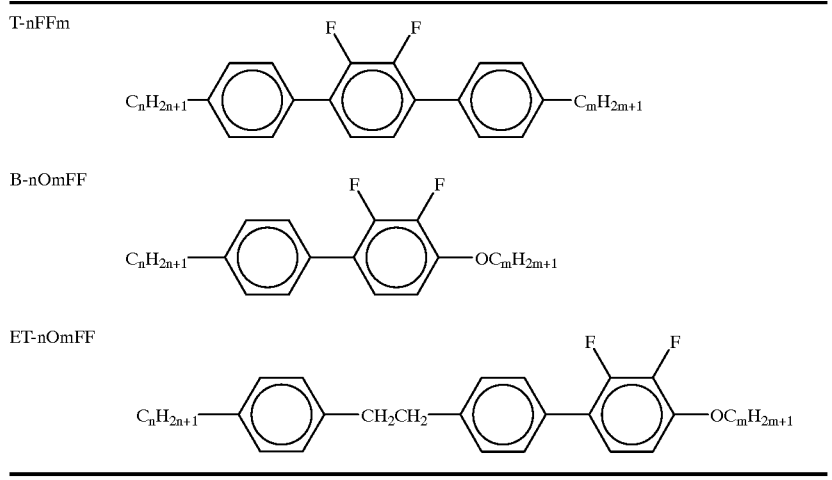

COMPARATIVE EXAMPLE 1

3,4,5,2'-Tetrafluoro-4'-(4-propylidenecyclohexyl)biphenyl 12.5 g of 4-(2,3',4',5'-tetrafluorobiphenyl-4-yl)cyclohexanone and 15.5 g of propyltriphenylphosphonium bromide were introduced into 150 ml of THF, and the mixture was cooled to −10° C. with stirring and under nitrogen. A solution of 4.5 g of potassium tert-butoxide in 150 ml of THF was then added dropwise with stirring at −10° C., and the mixture was then stirred at room temperature for a further 2 hours. The yellow suspension was then cooled to 10° C., and 200 ml of water were added. The organic phase was separated off, and the aqueous phase was extracted once with 100 ml of methyl tert-butyl ether. The combined organic extracts were washed once with 50 ml of water, dried using sodium sulfate, filtered and evaporated to a residue. The residue was purified by means of a silica-gel frit, and the eluate was evaporated to a residue, giving 3,4,5,2'-tetrafluoro-4'-(4-propylidenecyclohexyl)bi-phenyl.

COMPARATIVE EXAMPLE 2

3,4,5,2'-Tetrafluoro-4'-(4-fluoro-4-propylcyclohexyl)biphenyl 8.0 g of 3,4,5,2'-tetrafluoro-4'-(4-propylidenecyclohexyl)biphenyl in 16 ml of dichloromethane were introduced into a Teflon apparatus and cooled to −25° C. 80 ml of a 70% solution of hydrogen fluoride in pyridine were then added dropwise with stirring, and the mixture was stirred for 30 minutes at −25° C. and then for a further 1 hour at room temperature. The reaction solution was poured into a suspension of 10 g of sodium hydrogencarbonate and 200 g of ice-water. The mixture was then extracted with 3×80 ml of hexane. The combined organic extracts were washed once with 50 ml of sodium chloride solution, dried using sodium sulfate, filtered and evaporated to a residue. The crude product was purified by means of a silica-gel frit and the eluate was evaporated to a residue, giving 3,4,5,2'-tetrafluoro-4'-(4-fluoro-4-propylcyclohexyl)-biphenyl (C 73 N (48.8) I, Δε=15.3, Δn=+0.111).

The following compounds according to the invention were obtained analogously from the corresponding precursors:

| | $R^1$ | $Z^1$ | $L^2$ | $L^3$ | X |
|---|---|---|---|---|---|
| (1) | Ethyl | — | H | H | F |
| (2) | Propyl | — | F | H | F |
| (3) | Pentyl | — | F | F | F |
| (4) | Propyl | — | F | H | CN |
| (5) | Pentyl | — | F | F | CN |
| (6) | Propyl | — | F | H | $OCF_3$ |
| (7) | Pentyl | — | F | F | $OCF_3$ |
| (8) | Propyl | — | H | H | O-Propyl |
| (9) | Pentyl | — | F | H | Pentyl |
| (10) | Pentyl | — | F | F | Propyl |
| (11) | Propyl | — | F | H | $CH=CH_2$ |
| (12) | Pentyl | — | F | F | $(CH_2)_2CH=CH_2$ |
| (13) | Ethyl | —$CH_2$—$CH_2$— | H | H | F |
| (14) | Propyl | —$CH_2$—$CH_2$— | F | H | F |
| (15) | Pentyl | —$CH_2$—$CH_2$— | F | F | F |
| (16) | Propyl | —$CH_2$—$CH_2$— | F | H | CN |
| (17) | Pentyl | —$CH_2$—$CH_2$— | F | F | CN |
| (18) | Propyl | —$CH_2$—$CH_2$— | F | H | $OCF_3$ |
| (19) | Pentyl | —$CH_2$—$CH_2$— | F | F | $OCF_3$ |
| (20) | Propyl | —$CH_2$—$CH_2$— | H | H | Propyl |
| (21) | Pentyl | —$CH_2$—$CH_2$— | F | H | Pentyl |
| (22) | Pentyl | —$CH_2$—$CH_2$— | F | F | Propyl |

EXAMPLE 23

8-(3-Fluorophenyl)-1,4-dioxaspiro[4.5]decan-8-ol 48.6 g of magnesium turnings were wetted with 50 ml of THF, and a solution of 350 g of 1-bromo-3-fluorobenzene in 700 ml of THF was then added dropwise with stirring at such a rate that the reaction boiled gently. The mixture was then refluxed for a further 30 minutes and cooled to 10° C., and a solution of 312.4 g of cyclohexanedione monoethylene ketal and 600 ml of THF was added dropwise with stirring. During this addition, the reaction temperature rose to 60° C. The mixture was refluxed for a further 30 minutes and then cooled to room temperature. 800 ml of ammonium chloride solution were then added, and the mixture was neutralized using hydrochloric acid. The organic phase was separated off, and the aqueous phase was extracted once with 300 ml of methyl tert-butyl ether. The combined organic extracts were then washed once with 200 ml of sodium chloride solution, dried using sodium sulfate, filtered and evaporated to a residue, giving 8-(3-fluorophenyl)-1,4-dioxaspiro[4.5]decan-8-ol.

EXAMPLE 24
8-(3-Fluorophenyl)-1,4-dioxaspiro[4.5]dec-7-ene 513 g of 8-(3-fluorophenyl)-1,4-dioxaspiro[4.5]decan-8-ol, 1.8 l of xylene, 19 g of p-toluenesulfonic acid and 50 ml of ethylene glycol were boiled for 4 hours in a water separator. The reaction solution was cooled to room temperature and washed with 2×200 ml of water. The organic extracts were dried using sodium sulfate, filtered and evaporated to a residue, giving 8-(3-fluorophenyl)-1,4-dioxaspiro[4.5]dec-7-ene.

EXAMPLE 25
8-(3-Fluorophenyl)-1,4-dioxaspiro[4.5]decane 306.3 g of 8-(3-fluorophenyl)-1,4-dioxaspiro[4.5]dec-7-ene were dissolved in 3 l of THF, and 30 g of 5% Pd/C were added. The mixture was then hydrogenated at atmospheric pressure. The resultant solution was filtered and evaporated to a residue. The residue was recrystallized twice from 200 ml of hexane at −60° C., giving 8-(3-fluorophenyl)-1,4-dioxaspiro[4.5]decane.

EXAMPLE 26
8-(3-Fluoro-4-iodophenyl)-1,4-dioxaspiro[4.5]decane 121.0 g of 8-(3-fluorophenyl)-1,4-dioxaspiro[4.5]decane and 61.7 g of potassium tert-butoxide in 700 ml of THF were introduced into the apparatus and cooled to −100° C. 335.6 ml of a 15% solution of butyllithium in hexane were then added dropwise with stirring at −100° C., and the mixture was stirred at the same temperature for a further 30 minutes. A solution of 139.6 g of iodine in 300 ml of THF was then added dropwise with stirring at from −90 to −100° C., and the mixture was stirred for a further 30 minutes, allowed to warm to −25° C. and hydrolysed using 500 ml of water. 37% NaHSO$_3$ solution was then added until the mixture became colorless. The organic phase was then separated off, and the aqueous phase was extracted with 2×200 ml of methyl tert-butyl ether. The combined organic extracts were washed once with 200 ml of sodium chloride solution, dried using sodium sulfate, filtered and evaporated to a residue, giving 8-(3-fluoro-4-iodophenyl)-1,4-dioxaspiro[4.5]decane.

EXAMPLE 27
4-(3-Fluoro-4-iodophenyl)cyclohexanone 128.0 g of 8-(3-fluoro-4-iodophenyl)-1,4-dioxaspiro[4.5]decane and 320 ml of formic acid were dissolved in 750 ml of toluene and stirred at 25° C. overnight, the HCOOH phase was run off, diluted with 2 l of water and extracted twice with toluene, and the toluene phases were washed with water and sodium hydrogencarbonate solution until neutral, dried and evaporated. The crude product was recrystallized at −25° C. from 100 ml of hexane containing a few drops of ethyl acetate, giving 4-(3-fluoro-4-iodophenyl)cyclohexanone.

EXAMPLE 28
4-(4-Propylidenecyclohexyl)-2-fluoro-1-iodobenzene 44.95 g of 4-(3-fluoro-4-iodophenyl)cyclohexanone and 55.4 g of propyltriphenylphosphonium bromide were introduced into 250 ml of THF, and the mixture was cooled to −10° C. with stirring and under nitrogen. A solution of 15.8 g of potassium tert-butoxide in 150 ml of THF was then added dropwise at −10° C. with stirring, and the mixture was then stirred at room temperature for a further 2 hours. The yellow suspension was then cooled to 10° C., and 500 ml of water were added. The organic phase was separated off, and the aqueous phase was extracted once with 100 ml of methyl tert-butyl ether. The combined organic extracts were washed once with 100 ml of water, dried using sodium sulfate, filtered and evaporated to a residue. The residue was then purified by means of a silica-gel frit, and the eluate was evaporated to a residue, giving 4-(4-propylidenecyclohexyl)-2-fluoro-1-iodobenzene.

EXAMPLE 29
4-(4-Propylidenecyclohexyl)-2-fluoro-1-iodobenzene 8.6 g of 4-(4-propylidenecyclohexyl)-2-fluoro-1-iodobenzene in 30 ml of dichloromethane were introduced into a Teflon apparatus and cooled to −25° C. 2.5 ml of a 70% solution of hydrogen fluoride in pyridine were then added dropwise with stirring, and the mixture was stirred for 30 minutes at −25° C. and then for a further 1 hour at room temperature. The reaction solution was poured into a suspension of 10 g of sodium hydrogencarbonate and 200 g of ice-water. The mixture was then extracted with 3×80 ml of hexane. The combined organic extracts were washed once with 50 ml of sodium chloride solution, dried using sodium sulfate, filtered and evaporated to a residue. The crude product was purified by means of a silica-gel frit and the eluate was evaporated to a residue, giving 4-(4-propylidenecyclohexyl)-2-fluoro-1-iodobenzene.

EXAMPLE 30
2-Fluoro-4-(4-fluoro-4-propylcyclohexyl)-1-(4-propylphenylethynyl)benzene 3.64 g of 4-(4-propylidenecyclohexyl)-2-fluoro-1-iodobenzene, 1.44 g of 4-propylethynylbenzene, 100 ml of triethylamine, 0.05 g of copper(I) iodide and 0.025 g of bis(triphenylphosphine)palladium(II) chloride were combined and stirred for 3 hours at room temperature. The mixture was then poured into 500 ml of water, the organic phase was separated off, and the aqueous phase was extracted with 2×50 ml of methyl tert-butyl ether. The combined organic extracts were washed once with sodium chloride solution, dried using sodium sulfate, filtered and evaporated to a residue. The residue was purified by means of a flash column, and the combined fractions were evaporated to a residue, giving 2-fluoro-4-(4-fluoro-4-propylcyclohexyl)-1-(4-propylphenylethynyl)benzene (C 107 N, Δε=1.5, Δn=+0.267).

The following compounds are obtained analogously from the corresponding precursors:

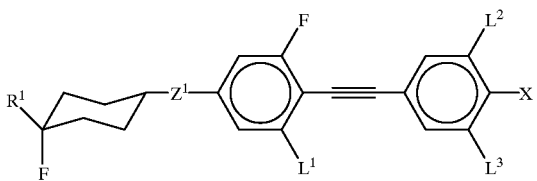

| | R$^1$ | Z$^1$ | L$^1$ | L$^2$ | L$^3$ | X |
|---|---|---|---|---|---|---|
| (31) | Ethyl | — | H | H | H | F |
| (32) | Propyl | — | F | F | H | F |

-continued

| | R¹ | Z¹ | L¹ | L² | L³ | X |
|---|---|---|---|---|---|---|
| (33) | Pentyl | — | F | F | F | F |
| (34) | Propyl | — | F | F | H | CN |
| (35) | Pentyl | — | F | F | F | CN |
| (36) | Propyl | — | F | F | H | OCF₃ |
| (37) | Pentyl | — | F | F | F | OCF₃ |
| (38) | Pentyl | — | H | H | H | Ethyl |
| | | | | | | Δε: 1.5, Δn: +0.253 |
| (39) | Pentyl | — | F | F | H | Propyl |
| (40) | Propyl | — | F | F | F | O-Pentyl |
| (41) | Ethyl | —COO— | H | H | H | F |
| (42) | Propyl | —COO— | F | F | H | F |
| (43) | Pentyl | —COO— | F | F | F | F |
| (44) | Propyl | —COO— | F | F | H | CN |
| (45) | Pentyl | —COO— | F | F | F | CN |
| (46) | Propyl | —COO— | F | F | H | OCHF₂ |
| (47) | Pentyl | —COO— | F | F | F | OCHF₂ |
| (48) | Propyl | —COO— | H | H | H | O-Propyl |
| (49) | Pentyl | —COO— | F | F | H | Pentyl |
| (50) | Pentyl | —COO— | F | F | F | Propyl |

| | R¹ | Z¹ | L¹ | L² | L³ | X |
|---|---|---|---|---|---|---|
| (51) | Ethyl | — | H | H | H | F |
| (52) | Propyl | — | F | F | H | F |
| (53) | Pentyl | — | F | F | F | F |
| (54) | Propyl | — | F | F | H | CN |
| (55) | Pentyl | — | F | F | F | CN |
| (56) | Propyl | — | F | F | H | OCF₃ |
| (57) | Pentyl | — | F | F | F | OCF₃ |
| (58) | Propyl | — | H | H | H | O-Propyl |
| (59) | Pentyl | — | F | F | H | Pentyl |
| (60) | Pentyl | — | F | F | F | Propyl |
| (61) | Ethyl | —COO— | H | H | H | F |
| (62) | Propyl | —COO— | F | F | H | F |
| (63) | Pentyl | —COO— | F | F | F | F |
| (64) | Propyl | —COO— | F | F | H | CN |
| (65) | Pentyl | —COO— | F | F | F | CN |
| (66) | Propyl | —COO— | F | F | H | OCHF₂ |
| (67) | Pentyl | —COO— | F | F | F | OCHF₂ |
| (68) | Propyl | —COO— | H | H | H | Propyl |
| (69) | Pentyl | —COO— | F | F | H | Pentyl |
| (70) | Pentyl | —COO— | F | F | F | Propyl |

| | R¹ | L¹ | L² | L³ | X |
|---|---|---|---|---|---|
| (71) | Ethyl | H | H | H | F |
| (72) | Propyl | F | F | H | F |
| (73) | Pentyl | F | F | F | F |
| (74) | Propyl | F | F | H | CN |
| (75) | Pentyl | F | F | F | CN |
| (76) | Propyl | F | F | H | OCF₃ |
| (77) | Pentyl | F | F | F | OCF₃ |
| (78) | Propyl | H | H | H | Propyl |
| (79) | Pentyl | F | F | H | Pentyl |
| (80) | Pentyl | F | F | F | Propyl |

EXAMPLE 81

A mixture is prepared which consists of:

| | Proportion by weight (%) |
|---|---|
| PCH-5F | 10.0 |
| PCH-6F | 8.0 |
| PCH-7F | 6.0 |
| CCP-20CF3 | 8.0 |
| CCP-30CF3 | 12.0 |
| CCP-40CF3 | 7.0 |
| CCP-50CF3 | 11.0 |
| BCH-3F.F | 12.0 |
| BCH-5F.F | 10.0 |
| ECCP-30CF3 | 5.0 |
| ECCP-50CF3 | 5.0 |
| CBC-33F | 2.0 |
| CBC-53F | 2.0 |
| CBC-55F | 2.0 | and whose physical data are shown in Table I.

TABLE I

| Cl.p. | +92° C. |
|---|---|
| Δε | +5.2 |
| Δn | +0.0969 |

After addition of 10% of the compound according to the invention 4-(4-fluoro-4-propylcyclohexyl)-1-(4-propylphenylethynyl)benzene (from Example 30), the following values were obtained:

| Cl.p. | +105° C. |
|---|---|
| Δε | +4.9 |
| Δn | +0.1132 |

The entire disclosure of all applications, patents and publications, cited above and below, and of corresponding German application No. 197 23 275.2, filed Jun. 4, 1997 is hereby incorporated by reference.

The preceding examples can be repeated with similar success by substituting the generically or specifically

What is claimed is:

1. Fluorocyclohexane derivatives of the formula I

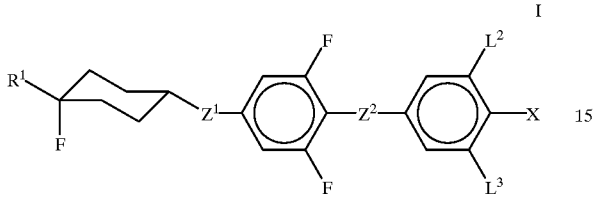

in which

X is alkyl or alkoxy having 1 to 10 carbon atoms which is unsubstituted or substituted by halogen, alkenyl or alkenyloxy having 2 to 10 carbon atoms which is unsubstituted or substituted by —CN, —CF$_3$ or —F, or is —CN, —F, —OCHF$_2$, —OCF$_3$, —OCHFCF$_3$ or —OCF$_2$CF$_3$, L$^1$, L$^2$ and L$^3$ are each, independently of one another, H or F, R$^1$ is H, an alkyl or alkenyl radical having 1–12 carbon atoms which is unsubstituted, monosubstituted by CN or CF$_3$ or substituted by halogen, where one or more non-adjacent CH$_2$ groups in these radicals may also, in each case independently of one another, be replaced by —O—, —S—, —CO—, —◊—, —CO—O—, —O—CO— or —O—CO—O—, Z$^1$ and Z$^2$ are each, independently of one another, —CO—O—, —O—CO—, —CH$_2$O—, —O—, —O—CH$_2$—, —CH$_2$CH$_2$—, —CH═CH—, —C≡C— or a single bond, with the proviso that compounds of the formula I in which L$^1$ is H and Z$^2$ is simultaneously a single bond are excluded.

2. Fluorocyclohexane derivatives of the formula I according to claim 1, characterized in that Z$^1$ is a single bond, C≡C or —CH$_2$—CH$_2$— and Z$^2$ is a single bond, —C≡C— or —CH$_2$—CH$_2$—.

3. Fluorocyclohexane derivatives according to claim 1, characterized in that X is unsubstituted alkyl or alkoxy having 1 to 7 carbon atoms, unsubstituted or fluoro-substituted alkenyl or alkenyloxy having 2 to 7 carbon atoms, F, CN, OCF$_3$ or OCHF$_2$.

4. Fluorocyclohexane derivatives according to claim 1, characterized in that R$^1$ is straight-chain alkyl or alkoxy having 1 to 10 carbon atoms or alkenyl having 2 to 10 carbon atoms.

5. Fluorocyclohexane derivatives according to claim 1, characterized in that L$^1$ and L$^2$ are simultaneously F, while Z$^1$ is a single bond or —CH$_2$—CH$_2$—.

6. A method of using compounds of the formula I according to claim 1 which comprises incorporating a compound of formula I in a liquid-crystalline medium.

7. Liquid-crystalline medium having at least two liquid-crystalline components, characterized in that it comprises at least one compound of the formula I of claim 1.

8. Medium according to claim 7, characterized in that it additionally comprises one or more compounds of the formula II:

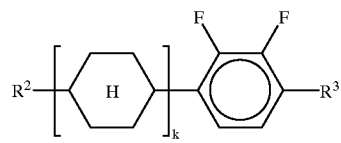

in which

R$^2$ and R$^3$ are each, independently of one another, H, an unsubstituted alkyl or alkenyl radical having up to 18 carbon atoms, in which one or more non-adjacent CH$_2$ groups may be replaced by a radical selected from the group consisting of —O—, —S—and —C≡C—, and k is 1 or 2.

9. Liquid-crystalline medium according to claim 7, characterized in that it additionally comprises one or more compounds of the formula III:

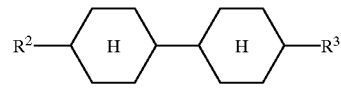

in which R$^2$ and R$^3$ are each, independently of one another, H, an unsubstituted alkyl or alkenyl radical having up to 18 carbon atoms, in which one or more non-adjacent CH$_2$ groups may be replaced by a radical selected from the group consisting of —O—, —S—and —C≡C—.

10. Liquid-crystalline medium according to claim 7, characterized in that it additionally comprises one or more compounds selected from the formulae V to IX:

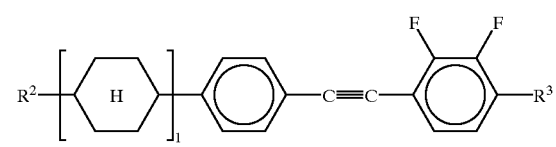

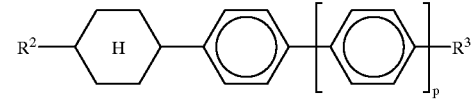

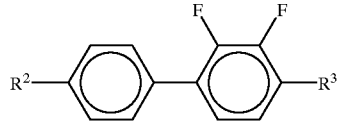

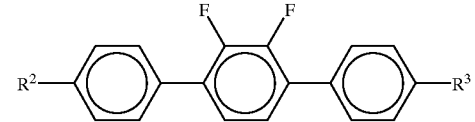

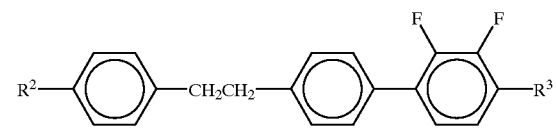

in which $R^2$ and $R^3$ are each, independently of one another,

H, an unsubstituted alkyl or alkenyl radical having up to 18 carbon atoms, in which one or more non-adjacent $CH_2$ groups may be replaced by a radical selected from the group consisting of —O—, —S— and —C≡C—; and l and p are each, independently of one another, 0 or 1.

11. Liquid-crystal display element, characterized in that it contains a liquid-crystalline medium according to claim 7.

12. Electro-optical display element, characterized in that it contains, as dielectric, a liquid-crystalline medium according to claim 7.

* * * * *